United States Patent
Omura et al.

(10) Patent No.: US 6,818,422 B2
(45) Date of Patent: Nov. 16, 2004

(54) SUBSTANCES K97-0239 AND PROCESS FOR PRODUCING THE SAME

(75) Inventors: Satoshi Omura, Tokyo (JP); Hiroshi Tomoda, Tokyo (JP)

(73) Assignees: Gakkou Houjin Kitasato Gakuen, Tokyo (JP); Japan Society for the Promotion of Science, Tokyo (JP)

( * ) Notice: Subject to any disclaimer, the term of this patent is extended or adjusted under 35 U.S.C. 154(b) by 0 days.

(21) Appl. No.: 10/398,578

(22) PCT Filed: Apr. 3, 2001

(86) PCT No.: PCT/JP01/02884

§ 371 (c)(1),
(2), (4) Date: Oct. 1, 2003

(87) PCT Pub. No.: WO02/081503

PCT Pub. Date: Oct. 17, 2002

(65) Prior Publication Data

US 2004/0043472 A1 Mar. 4, 2004

(51) Int. Cl.[7] ............................ C12P 17/18; C12N 1/20; C07D 489/00; C07D 487/02; C07D 487/04
(52) U.S. Cl. ................... 435/119; 435/253.5; 540/472
(58) Field of Search ............................... 435/119, 253.5; 540/472

(56) References Cited

FOREIGN PATENT DOCUMENTS

JP   2000-143629   5/2000

OTHER PUBLICATIONS

Satomi K. et al., "A New Cyclic Lipopeptide Antibiotic Enamido–nin", J. Antibiot. (1995) vol. 48, No. 2, pp. 185–187.
I. Namatame et al., Complete Inhibition of Mouse Macrophage–Derived Foam Cell Formation by Triacsin C[1].

*Primary Examiner*—Herbert J. Lilling
(74) *Attorney, Agent, or Firm*—Young & Thompson (57) ABSTRACT

A microorganism capable of producing substances K97-0239 comprising K97-0239A represented by the following formula [I]: and K97-0239B represented by the following formula [II]: is cultured in a medium and the substances K97-0239 thus accumulated in the medium are collected from the culture medium. The obtained substances have a low toxicity and specifically inhibit the foaming of macrophages. Owing to these characteristics, they are useful in preventing and treating human arteriosclerosis and diseases caused thereby.

6 Claims, 8 Drawing Sheets

SUBSTANCES K97-0239 AND PROCESS FOR PRODUCING THE SAME

BACKGROUND OF THE INVENTION

1. Field of the Invention

The present invention relates to a novel K97-0239 substance useful for prevention and treatment of arteriosclerosis and diseases caused therewith by specifically inhibiting generation of the foamy macrophage and production thereof.

2. Description of Related Arts

It is recently known that the life-style related diseases such as hyperlipidemia and obesity of adults are progressed to pathological conditions such as atherosclerosis, myocardial infarction, cerebral hemorrhage and cerebral apoplexy connecting directly with death. At present, statin series drugs such as pravastatin, fluvastatin, cerivastatin and atorvastatin are used as drugs for prevention and therapy of arteriosclerosis. These drugs have an effect for reducing cholesterol levels in blood by inhibiting HMG-CoA reductase, one of rate-limiting enzyme in cholesterol biosynthesis in vivo. However, arteriosclerosis is caused by complicated and complex etiology and drugs having different mechanism of action are strongly required.

In early lesion of atherosclerosis, machrophages infiltrating into the arterial endothelium recognize the denatured low density lipoprotein (hereinafter sometimes designates as LDL), which is generated by some denaturation such as oxidation and glucosylation of LDL, in the blood stream, incorporated endlessly and hydrolyze to generate free cholesterol and fatty acid, which are converted into cholesterol ester and triacylglycerol and accumulated in cytoplasm as lipid droplets. Then the macrophages are converted to foam cells to develop arteriosclerosis. Consequently, substances, which inhibits a process for forming the foamed macrophage, is expected to directly suppress development of arteriosclerotic lesion, but drugs, including statin series drugs, having such effect have not been known.

In such the actual condition, to provide substance, which inhibits the process for forming the foamed macrophage, is expected to contribute to the human health as a novel drug for directly acting arteriosclerotic lesion and suppressing the progress of disease.

An object of the present invention is to provide the novel K97-0239 substance satisfying such the expectation and the process for production thereof.

An another object of the present invention is to provide the drug for prevention and treatment of arteriosclerosis comprising K97-0239 substance as an active ingredient and the microorganism for production of said substance.

SUMMARY OF THE INVENTION

We have screened substance having inhibitory action for forming the foamy macrophage on metabolites produced by microorganisms, and found that a strain *Streptomyces* K97-0239, which was newly isolated from soil, produced, in the culture liquid, the substance having activity for inhibiting formation of the foamy macrophage. Then the substance having activity for inhibiting formation of the foamy macrophage was isolated and purified from said cultured mass, and we have found that the substance having such chemical structure has never known previously and designated the substance as K97-0239 substance.

The present invention has completed based on such knowledge, and relates to K97-0239 substance comprising K97-0239A substance represented by the following formula [I], and K97-0239B substance represented by the following formula [II], The present invention further relates to a process for production of novel K97-0239 substance comprising culturing a microorganism belonging to genus *Streptomyces* and having ability to produce K97-0239 substance, accumulating K97-0239 substance in a cultured mass and isolating K97-0239 substance from said cultured mass.

The present invention further relates to *Streptomyces* sp. K97-0239 which is the microorganism belonging to genus *Streptomyces* and having ability to produce K97-0239 substance.

The present invention still further relates to a microorganism which is *Streptomyces* sp. K97-0239 FERM BP-7514.

The microorganism having ability to produce K97-0239 substance represented by the above formula [I] and [II] (hereinafter designates as "K97-0239 substance producing microorganism") belongs to genus *Streptomyces*, and, for example, a strain *Streptomyces* sp. K97-0239, which was newly isolated from a soil sample collected in the Setagaya-ku, Tokyo by us, is an example of the strain used most effectively in the present invention.

Taxonomical properties of the strain K97-0239 are as follows.

(I) Morphological Properties

Vegetative mycelia grow well on various agar media and no fragmentation is observed. Aerial mycelia are abundantly grown on glycerol asparagine agar medium and inorganic salts-starch agar medium and show grayish color. On microscopic observation, chains of more than 20 spores were observed on the aerial mycelia, and the morphological form straight chain and size of spore is 0.7–0.9×1.0–1.3 μm with cylindrical form. Surface of the spore is smooth. No sclerotia, sporangia and zoospore are observed.

(II) Properties on Various Media

Culture properties of the producing strain of the present invention determined by the method of E. B. Shirling and D. Gottlieb (International Journal of Systematic Bacteriology, 16: 313, 1966) are shown in the following. Color tone was determined referring to Color Harmony Manual, 4th Ed. (Container Corporation of America Chicago, 1958) as a standard color, and color name as well as attached code number in the parenthesis. Unless otherwise noted, results are observation of cultures at 27° C. for 2 weeks on various media.

| Culturing properties | |
|---|---|
| Sucrose-nitrate agar medium | |
| Growth | good growth, pearl (3ba) |
| Reverse side | pearl (3ba) |
| Aerial mycelium | abundant, beige gray (3ih) |
| Soluble pigment | none |
| Glucose-asparagine agar medium | |
| Growth | moderate growth, fresh pink (3ca) |
| Reverse side | fresh pink (3ca) |
| Aerial mycelium | none |
| Soluble pigment | none |
| Glycerol-asparagine agar medium (ISP) | |
| Growth | good growth, pastel orange (4ic) |
| Reverse side | pastel orange (4ic) |
| Aerial mycelium | abundant growth, ashes (5fe) |
| Soluble pigment | none |
| Starch-inorganic salt agar medium (ISP) | |
| Growth | good growth, cream (2ca) |
| Reverse side | ivory (2db) |
| Aerial mycelium | abundant growth, lead gray (5ih) |
| Soluble pigment | none |
| Tyrosine agar medium (ISP) | |
| Growth | moderate growth, fresh pink (3ca) |
| Reverse side | fresh pink (3ca) |
| Aerial mycelium | moderate growth, orchid tint (10ba) |
| Soluble pigment | none |
| Oatmeal agar medium (ISP) | |
| Growth | good growth, light melon yellow (3ea) |
| Reverse side | light tan (3gc) |
| Aerial mycelium | abundant growth, ashes (5fe) |
| Soluble pigment | none |
| Yeast-malt extract agar medium (ISP) | |
| Growth | good growth, light amber (3ic) |
| Reverse side | light amber (3ic) |
| Aerial mycelium | abundant growth, lead gray (5ih) |
| Soluble pigment | none |
| Nutrient agar medium | |
| Growth | good growth, ivory (2db) |
| Reverse side | ivory (2db) |
| Aerial mycelium | none |
| Soluble pigment | none |
| Peptone-yeast-iron agar medium (ISP) | |
| Growth | good growth, dusty peach (3ec) |
| Reverse side | dusty peach (3ec) |
| Aerial mycelium | none |
| Soluble pigment | none |
| -continued | |
| Culturing properties | |
| Glucose-nitrate agar medium | |
| Growth | poor growth, pearl (3ba) |
| Reverse side | pearl (3ba) |
| Aerial mycelium | none |
| Soluble pigment | none |
| Grycerol-calcium malate agar medium | |
| Growth | good growth, dusty peach (3ec) |
| Reverse side | dusty peach (3ec) |
| Aerial mycelium | moderate growth, orchid tint (10ba) |
| Soluble pigment | none |
| Glucose-peptone agar medium | |
| Growth | moderate growth, light wheat (2ea) |
| Reverse side | light wheat (2ea) |
| Aerial mycelium | none |
| Soluble pigment | none |

Physiological Properties

| | | |
|---|---|---|
| (1) Formation of melanin pigment | | |
| (a) Tyrosine agar medium | | negative |
| (b) Peptpone-yeast-iron agar medium | | negative |
| (c) Tryptone-yeast liquid | | negative |
| (d) Simple gelatin medium (21–23° C.) | | positive |
| (2) Nitrate reduction | | positive |
| (3) Liquefaction of gelatin (21–23° C.) (simple gelatin medium) | | negative |
| (4) Starch hydrolysis | | positive |
| (5) Coagulation of defatted milk (37° C.) | | positive |
| (6) Peptonization of defatted milk (37° C.) | | positive |
| (7) Growth temperature | | 10–38° C. |
| (8) Utilization of carbon sources (Pridham-Gottlieb agar medium) | | |
| Utilize | glucose, arabinose | |
| Slightly utilize | fructose, sucrose | |
| Not utilize | xylose, mannitol, rhamnose, melibiose, inositol, raffinose | |
| (9) Decomposition of cellulose | | negative |

(IV) Composition of Cell Wall 2,6-diaminopimelic acid of cell wall is LL type.

Taxonomical properties of the strain of the present invention are summarized as follows.

2,6-diaminopimelic acid in the cell wall is LL type. Morphology of the spore chain is straight, forming with long spore chain and smooth spore surface. Various properties on the culture are exhibiting pale yellow color tone with grayish aerial mycelia. Production of melanin pigment is observed on the simple gelatin medium (cultured at 21–23° C.). No other pigments formation was observed.

The present strain exhibiting the above morphological properties, culture properties and pysiological properties was identified as the strain belonging to genus *Streptomyces*, and was thought to be the strain belonging to the gray series in the classification by Pridham and Tresner (Bergey's Manual of Determinative Bacteriology, 8th ED., page 748–829, 1974). The strain was deposited as *Streptomyces* sp. K97-0239 in International Patent Organism Depository, National Institute of Advanced Industrial Science and Technology, AIST Tsukuba Central 6, 1-1, Higashi 1-chome, Tsukuba-shi, Ibaraki-ken, 305-8566 Japan on Mar. 19, 2001 under the Budapest Treaty relating to international approval for deposition of microorganism on the patent procedure, and permanent depository number is FERM BP-7514.

Preferable example of K97-0239 substance producing strain used in the present invention is the strain *Streptomyces* sp. K97-0239. However, since the morphological properties of microorganisms are generally very easily mutated and are not constant. Natural mutation or artificial mutation generally performed by ultraviolet irradiation or chemical mutagens such as N-methyl-N'-nitro-N-nitrosoguanidine and ethyl methansulfonate, are well known. The strain belonging to genus *Streptomyces* and having ability to produce K97-0239 substance, including the artificial mutants as well as natural mutants, can be used in the present invention.

In addition, all strains belonging to genus *Streptomyces* and having ability to produce K97-0239 substance represented by the formula [1] and [11] hereinbefore (hereinafter designate as "K97-0239 substance", if not specified) including strains mutated by cell engineering technology such as cell fusion, gene manipulation, etc., can be used in the present invention.

In production of K97-0239 substance of the present invention, at first, K97-0239 substance producing strain belonging to genus *Streptomyces* is cultured in a medium. Nutrient sources preferable used for production of K97-0239 substance are assimilable carbon sources for microorganism, digestible nitrogen sources and, if necessary, inorganic salts and vitamins can be used as nutrient medium.

Examples of carbon sources are sugars such as glucose, fructose, maltose, lactose, galactose, dextrin and starch and vegetable oils such as soybean oil, and are used independent or in combination.

Examples of nitrogen sources are peptone, yeast extract, meat extract, soybean powder, cotton seed powder, corn steep liquor, malt extract, casein, amino acids, urea, ammonium salts and nitrates, and are used independent or in combination. If necessary, salts such as phosphate, magnesium, calcium, sodium and potassium, heavy metal salts such as iron, manganese, copper, cobalt and zinc, vitamins and other materials preferable for production of K97-0239 substance are optionally added.

In the culture, anti-foaming agents such as liquid paraffin, animal oil, vegetable oil, silicone oil, surface active agents, etc. can be added if necessary when foaming occurs. The culture can be performed by liquid or solid culture if containing the above nutrient sources, and generally the culture is preferably performed by the liquid culture. In the small culture, the culture using flask is preferable.

In the large scale production using the large tank, in order to prevent delay of growth of microorganism in the production process, the production strain is inoculated and cultured initially in relatively small amount of culture medium, subsequently the cultured mass is transferred into the large tank and cultivation is preferably continued. In this case, compositions of the medium used in the pre-culture and the medium used in the production culture can be identical or different if necessary.

In the culture under aeration stirring condition, conventional means, for example, agitation using propeller and other mechanical stirring, rotation or shaking in fermenter, treating with pumping and blowing air can be applied. Air for aeration should be sterilized. Culturing temperature can be applied within ranges in the production of K97-0239 substance by K97-0239 substance producing strain, and the cultivation is performed usually at 20–30° C., preferably at 27° C. Culturing pH is usually pH 5–8, preferably about pH 7. Culturing time depends on culturing condition and is usually for 3 days.

The thus obtained K97-0239 substance exists in the cultured microorganism cells and the culture filtrate. Isolation of K97-0239 substance from the cultured mass can be performed by extracting the whole cultured mass with water miscible organic solvent such as acetone, distilling off the organic solvent from the extract in vacuo, and extracting the residue with water immiscible organic solvent such as ethyl acetate.

In addition to the above extraction procedure, conventional methods used for isolation of fat-soluble substances such as adsorption chromatography, gel filtration chromatography, thin-layer chromatography, centrifugal counter current chromatography and high performance liquid chromatography can be used optionally in combination or repeatedly to isolate and purify K97-0239 substance.

Physicochemical properties of K97-0239A substance of the present invention are explained hereinbelow.

Figure 1:
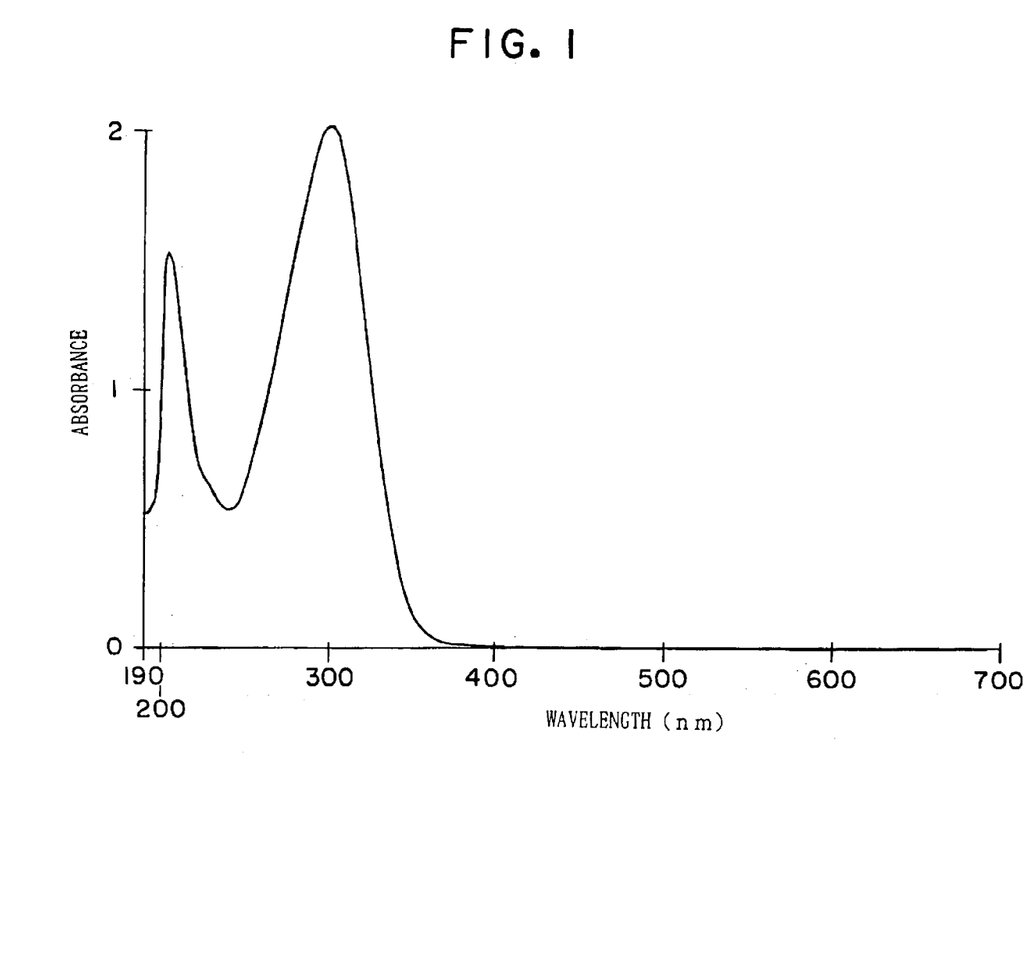
FIG. 1 shows ultraviolet absorption spectrum (in methanol) of K97-0239A substance of the present invention.
Figure 2:
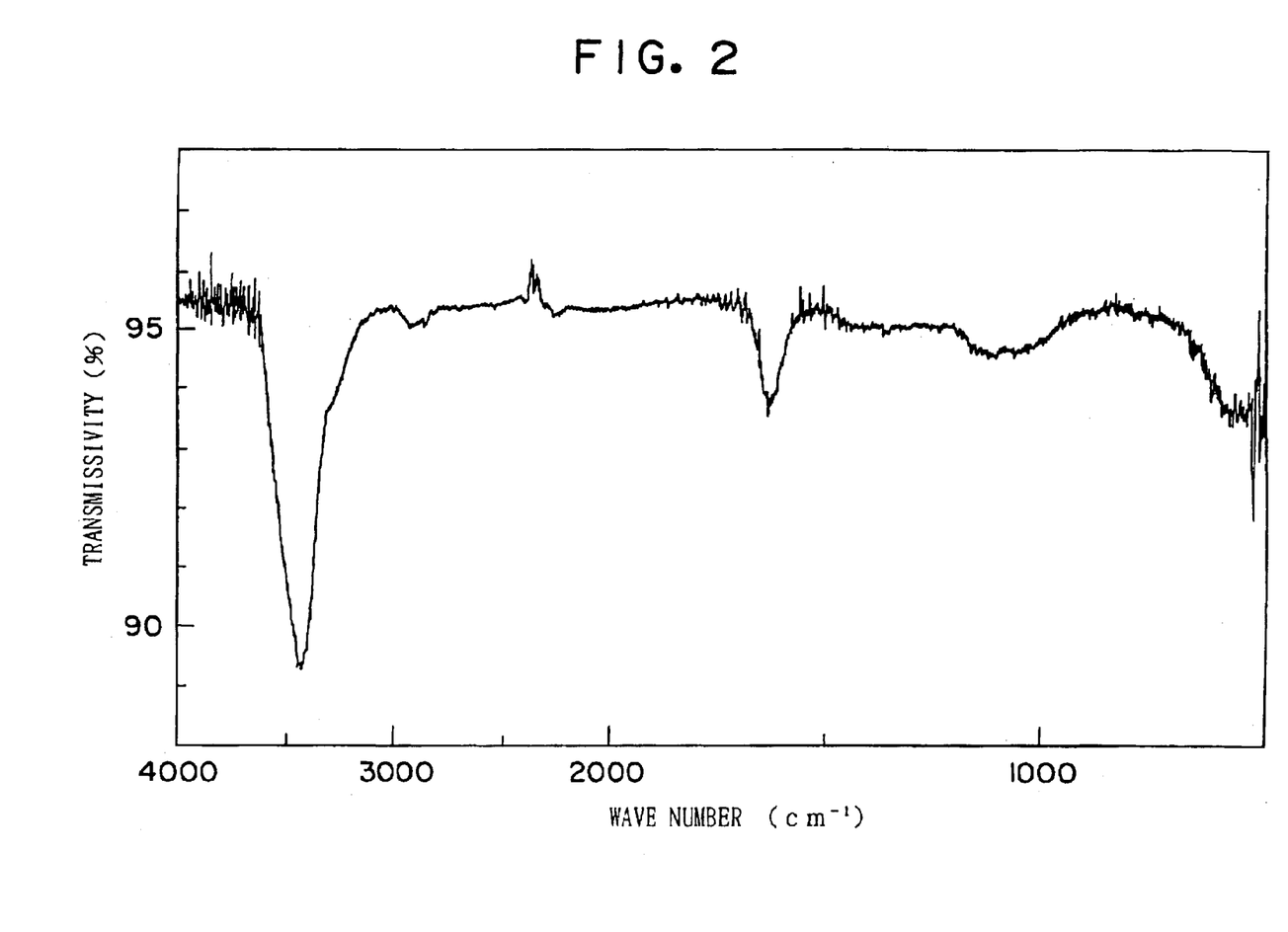
FIG. 2 shows Infrared absorption spectrum (KBr tablet) of K97-0239A substance of the present invention.
Figure 3:
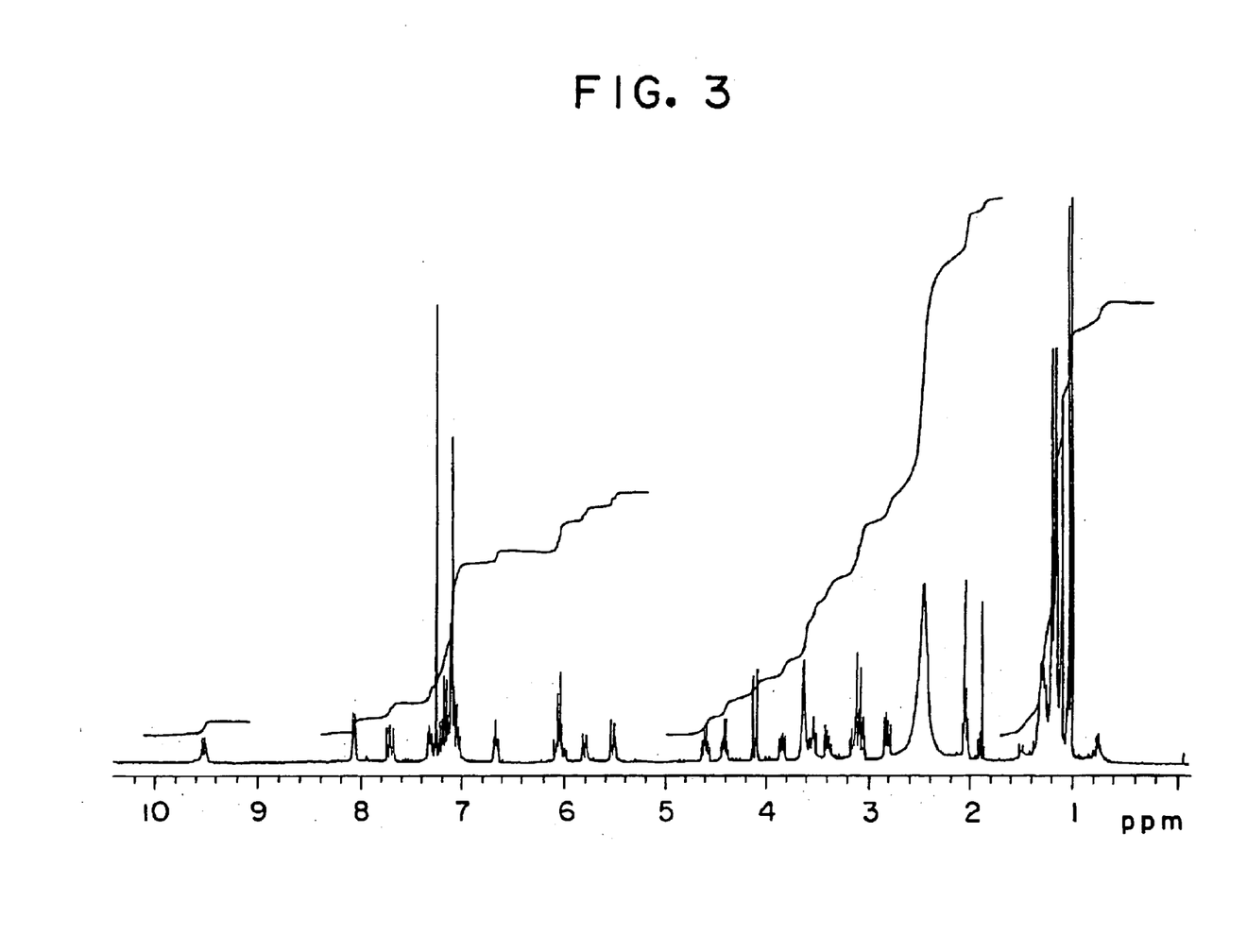
FIG. 3 shows $^1$H-nuclear magnetic resonance spectrum (deuteriochloroform:deuterio-DMSO=40:1) of K97-0239A substance of the present invention.
Figure 4:
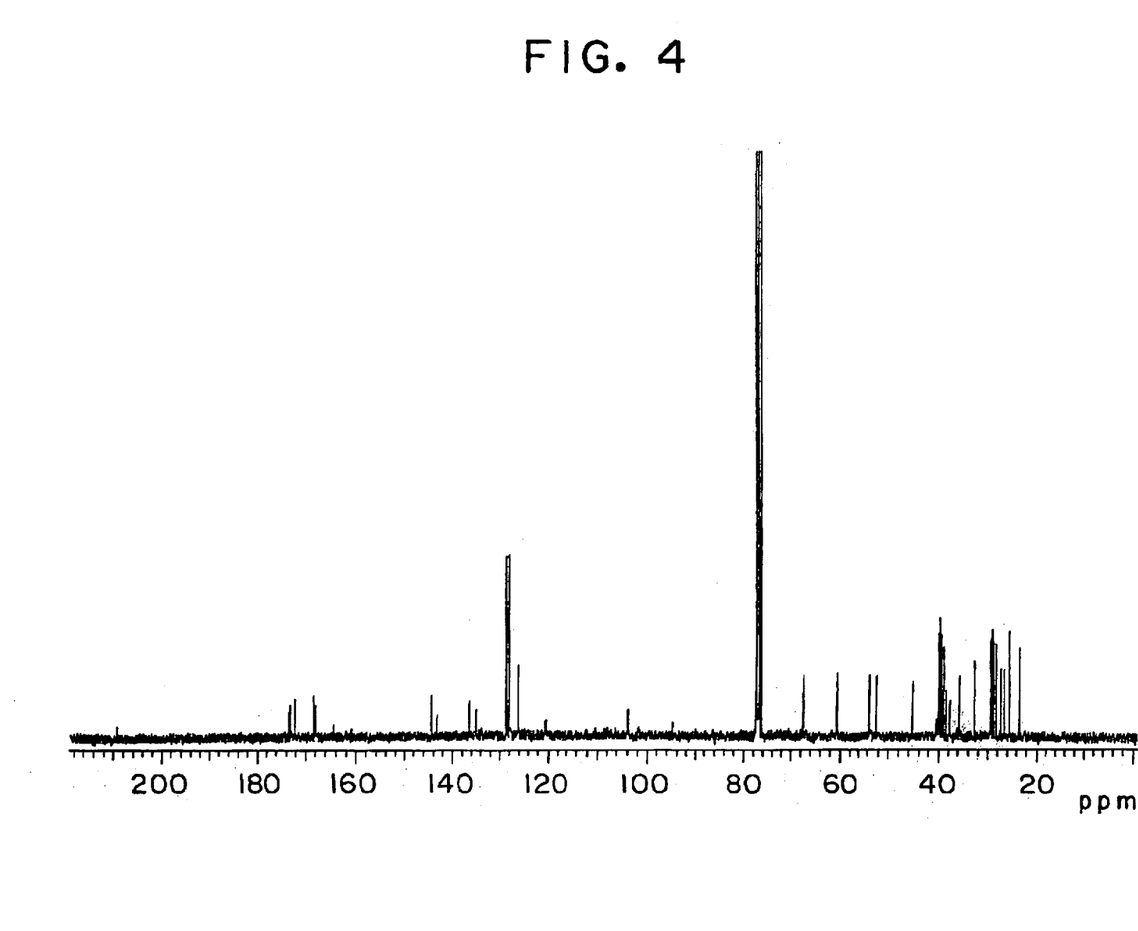
FIG. 4 shows $^{13}$C-nuclear magnetic resonance spectrum (deuteriochloroform:deuterio-DMSO=40:1) of K97-0239A substance of the present invention.

(1) Appearance: white powder
(2) Molecular weight: 707 (fast atom bombardment mass spectrometry)
(3) Molecular formula: $C_{37}H_{53}N_7O_7$
(4) Specific rotation: $[\alpha]_D^{22}=+164°$ (c=0.1, methanol)
(5) Ultraviolet absorption spectrum (in methanol): as shown in FIG. 1, maximum absorption at 204 nm (log $\epsilon$=15600) and 300 nm (log $\epsilon$=25700)
(6) Infrared absorption spectrum (KBr Tablet): as shown in FIG. 2, maximum absorption at 3442, 1633, 1525, 1367, 1242, 1167 cm$^{-1}$
(7) $^1$H-nuclear magnetic resonance spectrum (deuteriochloroform:duterio-DMSO=40:1): as shown in FIG. 3. Chemical shift (ppm) is shown in Table 1.
(8) $^{13}$C-nuclear magnetic resonance spectrum (deuteriochloroform:duterio-DMSO=40:1): as shown in FIG. 4. Chemical shift (ppm) is shown in Table 1.
(9) Solubility in solvent: soluble in methanol, benzene, chloroform and ethyl acetate and slightly soluble in water and hexane.
(10) Color reaction: positive for sulfuric acid and phosphormolybdic acid.
(11) Grouping for acidic, neutral and basic: Neutral substance.

TABLE 1

| No. | $^{13}$C | $^1$H |
|---|---|---|
| 1 | 164.40 | |
| 2 | 120.51 | 5.81 (1 H, d, J = 15.5 Hz) |
| 3 | 143.40 | 7.19 (1 H, dd, J = 15.5, 9.5 Hz) |
| 4 | 128.15 | 6.06 (1 H, dd, J = 15.0, 9.5 Hz) |
| 5 | 144.63 | 6.03 (1 H, dd, J = 15.0, 6.5 Hz) |
| 6 | 32.71 | 2.05 (2 H, dd, J = 13.0, 6.5 Hz) |
| 7 | 28.39 | 1.30 (2 H, m) |
| 8 | 29.26 | 1.17 (2 H, m) |
| 9 | 29.06 | 1.17 (2 H, m) |
| 10 | 28.78 | 1.17 (2 H, m) |
| 11 | 25.46 | 1.28 (2 H, m) |
| 12 | 39.06 | 1.30 (1 H, m) |
|  |  | 1.60 (1 H, m) |
| 13 | 67.37 | 3.62 (1 H, m) |
| 13-OH |  | 7.16 (1 H, m) |
| 14 | 23.26 | 1.04 (3 H, d, J = 6.3 Hz) |
| 16 | 45.15 | 3.10 (1 H, d, J = 13.5 Hz) |
|  |  | 4.10 (1 H, d, I = 13.5 Hz) |
| 17 | 168.25 |  |
| 18 |  | 7.18 (1 H, d, J = 9.0 Hz) |
| 19 | 53.83 | 4.60 (1 H, ddd, J = 10.0, 9.0, 7.0 Hz) |
| 20 | 172.15 |  |
| 21 |  | 8.08 (1 H, d, J = 6.8 Hz) |
| 22 | 52.33 | 4.41 (1 H, ddd, J = 7.0, 7.0, 6.8 Hz) |
| 23 | 173.17 |  |
| 24 |  | 7.32 (1 H, dd, J = 7.5, 5.5 Hz) |
| 25 | 38.55 | 3.14 (1 H, ddd, J = 14.5, 5.5, 3.5 Hz) |
|  |  | 3.84 (1 H, ddd, J = 14.5, 7.5, 1.5 Hz) |
| 26 | 60.47 | 3.63 (1 H, m) |
| 27 |  | 7.12 (1 H, m) |
| 28 | 77.70 |  |
| 29 | 27.14 | 1.21 (3 H, s) |
| 30 | 26.55 | 1.12 (3 H, s) |
| 31 | 173.28 |  |
| 32 | 37.67 | 3.40 (1 H, ddd, J = 14.5, 7.0, 6.8 Hz) |
|  |  | 3.53 (1 H, ddd, J = 14.5, 7.0, 6.0 Hz) |

TABLE 1-continued

| No. | $^{13}$C | $^1$H |
|---|---|---|
| 33 | | 6.67 (1 H, dd, J = 6.8, 6.0 Hz) |
| 34 | 167.98 | |
| 35 | 103.83 | 5.53 (1 H, d, J = 14.0 Hz) |
| 36 | 135.13 | 7.71 (1 H, dd, J = 14.0, 10.5 Hz) |
| | | 9.52 (1 H, d, J = 10.5 Hz) |
| 38 | 35.67 | 2.81 (1 H, dd, J = 14.0, 7.0 Hz) |
| | | 3.09 (1 H, dd, J = 14.0, 10.0 Hz) |
| 39 | 136.48 | |
| 40 | 128.71 | 7.10 (2 H, d, J = 7.0 Hz) |
| 41 | 128.22 | 7.11 (2 H, dd, J = 7.0, 7.0 Hz) |
| 42 | 126.34 | 7.04 (1 H, dd, J = 7.0, 7.0 Hz) |

Proviso that alphabetical letters indicate the following means: d: doublet, dd: double doublet, ddd: double double doublet, J: spin coupling constant, m: multiplet, and s: singlet.

As described hereinabove, as the results of examining various physicochemical properties and spectral data of K97-0239A substance, K97-0239A substance was determined as having chemical structure represented by the formula [I].

[I]

Physicochemical properties of K97-0239B substance of the present invention are explained hereinbelow.

Figure 5:
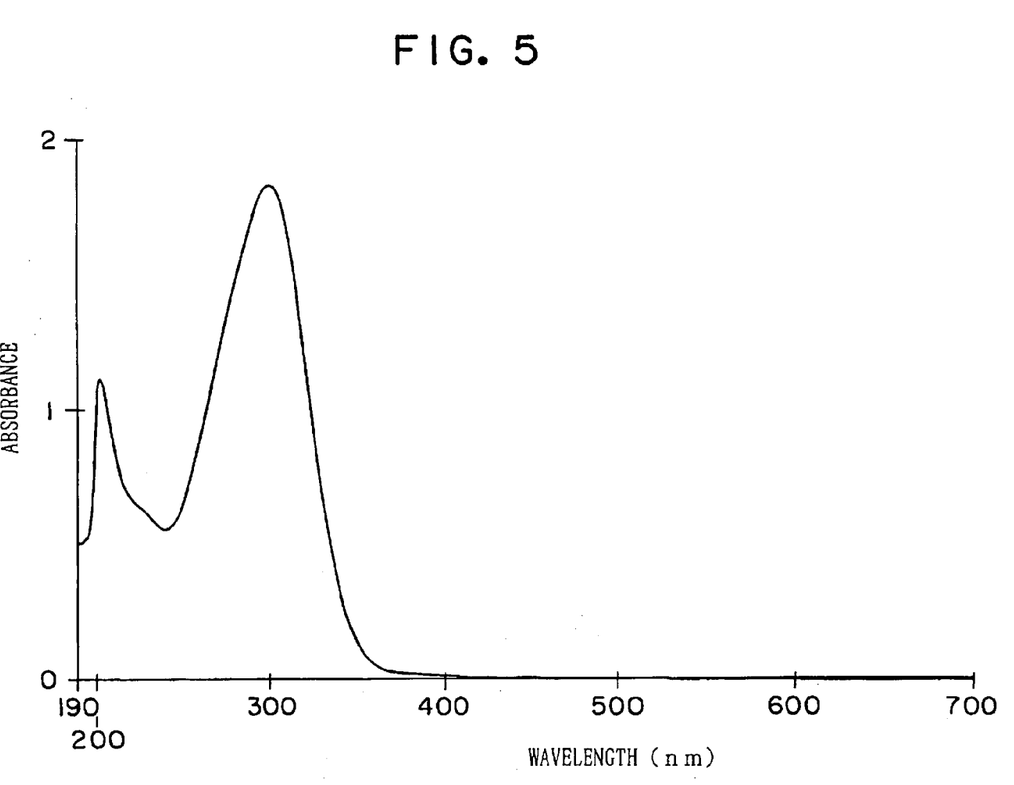
FIG. 5 shows ultraviolet absorption spectrum (in methanol) of K97-0239B substance of the present invention.
Figure 6:
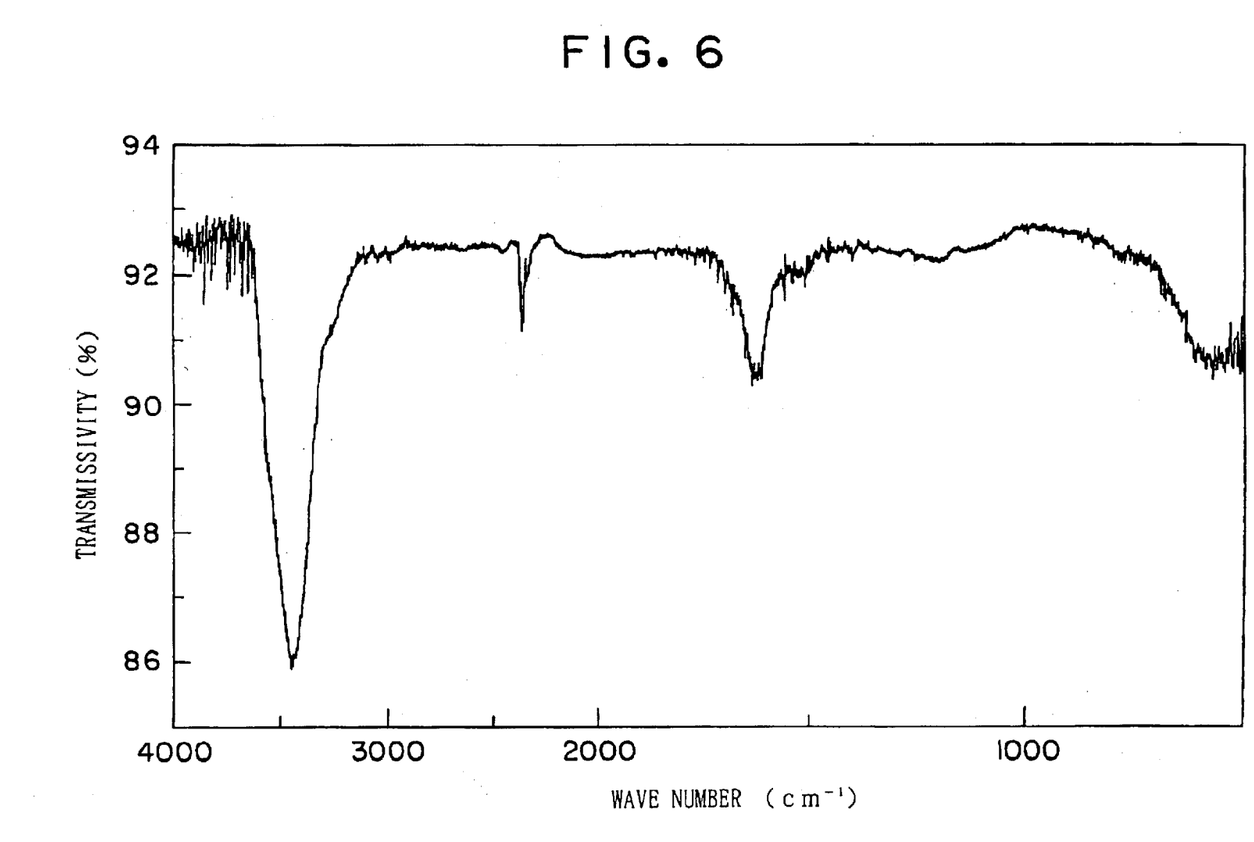
FIG. 6 shows Infrared absorption spectrum (KBr tablet) of K97-0239B substance of the present invention.
Figure 7:
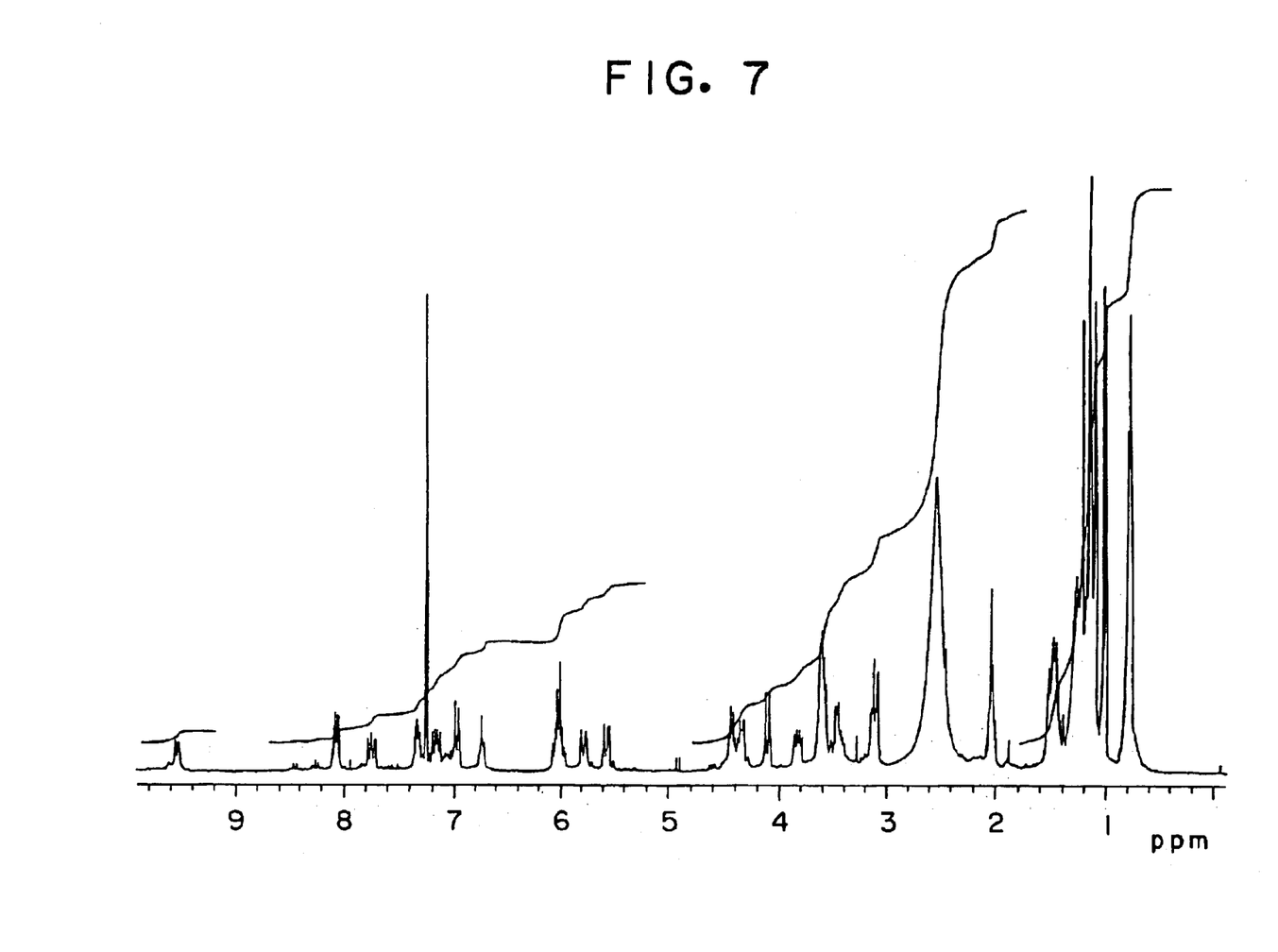
FIG. 7 shows $^1$H-nuclear magnetic resonance spectrum (deuteriochloroform:deuterio-DMSO=40:1) of K97-0239B substance of the present invention.
Figure 8:
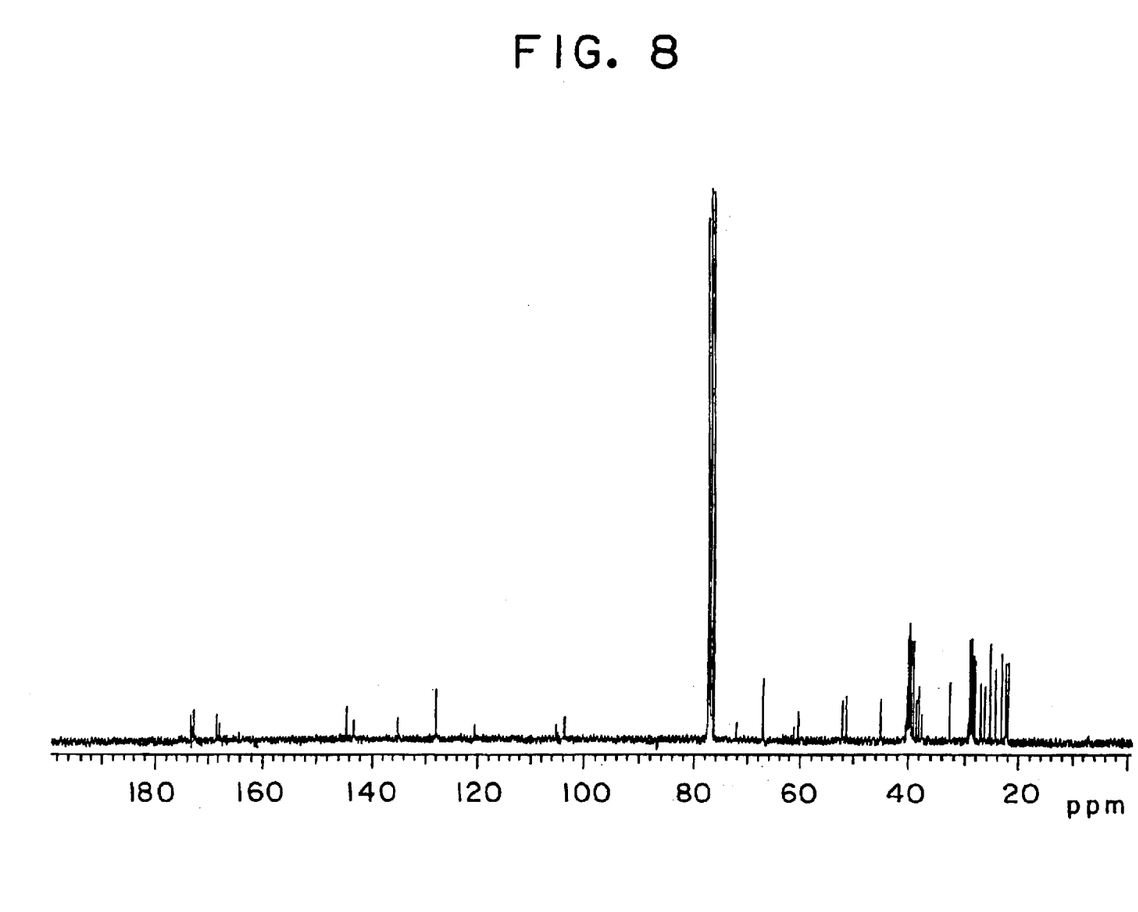
FIG. 8 shows $^{13}$C-nuclear magnetic resonance spectrum (deuteriochloroform:deuterio-DMSO=40:1) of K97-0239B substance of the present invention.

(1) Appearamce: white powder
(2) Molecular weight: 673 (fast atom bombardment mass spectrometry)
(3) Molecular formula: $C_{34}H_{55}N_7O_7$
(4) Specific rotation: $[\alpha]_D^{22}$=+68° (c=0.1, methanol)
(5) Ultraviolet absorption spectrum (in methanol): as shown in FIG. 5, maximum absorption at 204 nm (log ε=14800) and 300 nm (log ε=24500)
(6) Infrared absorption spectrum (KBr Tablet): as shown in FIG. 6, maximum absorption at 3440, 1637, 1618, 1518, 1400, 1255, 1194 cm$^{-1}$
(7) $^1$H-nuclear magnetic resonance spectrum (deuteriochloroform:duterio-DMSO=40:1): as shown in FIG. 7. Chemical shift (ppm) is shown in Table 2.
(8) $^{13}$C-nuclear magnetic resonance spectrum (deuteriochloroform:duterio-DMSO=40:1): as shown in FIG. 8. Chemical shift (ppm) is shown in Table 2.
(9) Solubility in solvent: soluble in methanol, benzene, chroloform and ethyl acetate and slightly soluble in water and hexane.
(10) Color reaction: positive for sulfuric acid and phosphormolybdic acid.
(11) Grouping for acidic, neutral and basic: Neutral substance.

TABLE 2

| No. | $^{13}$C | $^1$H |
|---|---|---|
| 1 | 164.36 | |
| 2 | 120.53 | 5.78 (1 H, d, J = 15.5 Hz) |
| 3 | 143.28 | 7.16 (1 H, dd, J = 15.5, 9.5 Hz) |
| 4 | 128.09 | 6.02 (1 H, dd, J = 15.0, 9.5 Hz) |
| 5 | 144.51 | 6.00 (1 H, dd, J = 15.0, 6.0 Hz) |
| 6 | 32.63 | 2.03 (2 H, dd, J = 13.0, 6.0 Hz) |
| 7 | 28.32 | 1.30 (2 H, m) |
| 8 | 29.20 | 1.16 (2 H, m) |
| 9 | 28.99 | 1.16 (2 H, m) |
| 10 | 28.70 | 1.16 (2 H, m) |
| 11 | 25.40 | 1.30 (2 H, m) |
| 12 | 39.00 | 1.30 (1 H, m) |
| | | 1.60 (1 H, m) |
| 13 | 67.23 | 3.61 (1 H, m) |
| 13-OH | | 7.32 (1 H, m) |
| 14 | 23.20 | 1.03 (3 H, d, J = 6.3 Hz) |
| 16 | 45.15 | 3.11 (1 H, d, J = 14.0 Hz) |
| | | 4.11 (1 H, d, J = 14.0 Hz) |
| 17 | 168.25 | |
| 18 | | 6.97 (1 H, d, J = 10.0 Hz) |
| 19 | 51.45 | 4.34 (1 H, ddd, J = 10.0, 10.0, 7.0 Hz) |
| 20 | 173.26 | |
| 21 | | 8.07 (1 H, d, J = 6.8 Hz) |
| 22 | 52.05 | 4.43 (1 H, ddd, J = 7.0, 7.0, 6.8 Hz) |
| 23 | 173.00 | |
| 24 | | 7.33 (1 H, dd, J = 7.5, 5.5 Hz) |
| 25 | 38.47 | 3.11 (1 H, dd, J = 14.0, 5.0 Hz) |
| | | 3.83 (1 H, dd, J = 14.0, 7.8 Hz) |
| 26 | 60.36 | 3.58 (1 H, m) |
| 27 | | 7.04 (1 H, m) |
| 28 | 76.95 | |
| 29 | 27.08 | 1.22 (3 H, s) |
| 30 | 26.44 | 1.12 (3 H, s) |
| 31 | 172.66 | |
| 32 | 37.57 | 3.45 (1 H, ddd, J = 14.5, 7.0, 6.0 Hz) |
| | | 3.60 (1 H, m) |
| 33 | | 6.74 (1 H, dd, J = 6.0, 6.0 Hz) |
| 34 | 167.83 | |
| 35 | 103.81 | 5.57 (1 H, d, J = 14.0 Hz) |
| 36 | 135.08 | 7.75 (1 H, dd, J = 14.0, 10.5 Hz) |
| 37 | | 9.54 (1 H, d, J = 10.5 Hz) |
| 38 | 38.14 | 1.50 (1 H, m) |
| | | 3.10 (1 H, dd, J = 14.0, 10.0 Hz) |
| 39 | 24.38 | 1.49 (1 H, m) |
| 43 | 22.06 | 0.78 (3 H, d, J = 6.5 Hz) |
| 44 | 22.32 | 0.80 (3 H, d, J = 6.0 Hz) |

Proviso that alphabetical letters indicate the following means: d: doublet, dd: double doublet, ddd: double double doublet, J: spin coupling constant, m: multiplet, and s: singlet.

As described hereinabove, as the results of examining various physicochemical properties and spectral data of K97-0239B substance, K97-0239B substance was determined as having chemical structure represented by the formula [II].

[II]

Inhibitory action of K97-0239 substance of the present invention on cholesteryl ester and lipid droplets formation in mouse peritoneal macrophage is explained.

Cholesteryl ester formation and lipid droplets formation in mouse peritoneal machrophage were performed according to a method of Namatame et al. (J. Biochem. 125: 319–327, 1999).

Machrophages isolated from mouse peritoneal fluid were suspended at $2.0 \times 10^6$ cells/ml in Dulbeco's modified Eagle's medium containing 6.8% lipoprotein deficient serum (6.8% LPDS-DMEM) and aliquots (0.25 ml) were dispensed into a 48-well microplate (Corning Co.) or a slide chamber (Nunc Co.).

The plate was incubated in a humidified 5% $CO_2$ atmosphere incubator at 37° C. for 2 hours, after which each plate was washed with Hank's solution to remove the unattaced cells. The plate was incubated in 6.8% LPDS-DMEM for 1 hour, and K97-0239 substances (2.5 μl methanol solution), liposome [consisting of phosphatidylcholine/phosphatidylserine/dicetylphosphate/cholesterol=10:10:2:15 (nmol) in 10 μl of 0.3 M glucose] and [1-$^{14}$C] oleic acid (5 μl, 0.05 μCi, 1 nmol) were added therein, then incubated further for 14 hours.

After the incuvation, supernatant was removed and the intracellular neutral lipids were extracted twice with adding hexane 0.6 ml and isopropanol 0.4 ml. The mixture was concentrated, spotted on TLC plate (silica gel plate, Merck Co., thickness 0.5 mm) and developed with a mixed solvent of hexane/diethyl ether/acetic acid (70:30:1:v/v). The separated [$^{14}$C] cholesteryl olate and [$^{14}$C] triacylglycerol were quantitatively assayed using radio scanner (Ambis Co.). Results indicated that K97-0239 substance relatively selectively inhibited generation of [$^{14}$C] cholesteryl olate and $IC_{50}$ value is 1.5 μM for K97-0239A substance and 1.7 μM for K97-0239B substance. Generation of [$^{14}$C] triacylglycerol was inhibited about 30% by 15 μM of K97-0239A substance and about 50% by 15 μM of K97-0239B substance.

Inhibition of lipid droplets generated in cells was observed as follows. Macrophages was incubated with K97-0239 substance and the liposome hereinabove described in 6.8% LPDS-DMEM for 14 hours. The lipid droplets and nuclei were double stained with oil red o and hematoxylin, and observed by optical microscope (Olympus Optical Co., Japan). Results indicated that lipid droplets accumulated in cytoplasma under 10 μM of K97-0239 substance were decreased to about 50% as compared with no drug addition (control).

Next, toxicity test of K97-0239 substance of the present invention was explained hereinbelow.

No toxicity of K97-0239 substance was observed for growth of mouse peritoneal machrophage at the final concentration of 20 μM. No toxicity was noted when 100 mg/kg of K97-0239 substance was administered perorally in mouse.

BEST MODE FOR CARRYING OUT THE INVENTION

The present invention is explained by mentioning examples, but is not limited within the example.

A 50 ml test tube containing a medium containing glucose 0.1%, starch 2.4%, peptone 0.3%, meat extract 0.3%, yeast extract 0.5% and $CaCO_3$ 0.4% dissolved in tap water 10 ml (adjusted to pH 7.0) was sealed with sponge plug and sterilized by steam. Streptomyces sp. K97-0239 (FERM BP-7514) grown on the agar medium was aseptically inoculated by a platinum loop and shake cultured at 27° C. for 3 days to obtain the seed culture liquid.

A 500 ml Erlenmeyer flask containing a medium containing glucose 0.1%, starch 2.4%, peptone 0.3%, meat extract 0.3%, yeast extract 0.5% and $CaCO_3$ 0.4% dissolved in tap water 100 ml (adjusted to pH 7.0) was sealed with sponge and steam sterilized. The above seed culture liquid 2 ml was aseptically inoculated thereto and shake cultured at 27° C. for 3 days to obtain second seed culture liquid.

A medium containing soluble starch 4.0%, hyprotoast meal 2.0%, $K_2HPO_4$ 0.05%, $FeSO_4 \cdot 7H_2O$ 0.05%, KCl 0.03% and 0.1 N sodium thiosulfate 32 μg/lit. dissolved in tap water 20 lit. (adjusted to pH 6.5) was poured into 30 lit. jar-fermenter (in one jar-fermenter, total 5 sets were prepared) and steam sterilized. The above each of second seed culture liquid 400 ml was aseptically inoculated thereto and cultured at 27° C. for 3 days with aeration.

After cultivation, the cultured liquid 100 lit. was centrifuged by Sharpless centrifugal machine to obtain the separated mycelia, which were treated with acetone 20 lit., filtered, concentrated the filtrate in vacuo to distilled off acetone to obtain aqueous solution. The aqueous solution was extracted with ethyl acetate 10 lit. The extract was concentrated in vacuo to obtain crude substance 16.9 g. The crude substance was charged on a column of ODS gel (200 g, Pegasil, Senshu Kagaku Co.) and column chromatography was performed eluting with 30%–100% aqueous acetonitrile (linear density gradient).

Each fraction was fractionated in each 12.5 ml, collected 50%–65% acetonitrile fractions containing active ingredient and dried in vacuo to obtained crude active brown colored substance 396 mg. The crude substance was further charged on a column of LH-20 (50 g, Pharmacia Inc.) and performed column chromatography eluting with methanol. Each fraction was fractionated in 1 ml eluate, collected 49–58 ml eluting fractions containing the active ingredient, and dried in vacuo to obtain crude active brown color substance 131 mg.

The crude substance was divided into 20 fractions and each fraction was separated and purified by using HPLC. Equipment used was Model PU-1580 (JASCO Co.). Column used was YMC-Pack S-5 (ODS resin, 20×250 mm, Yamamura Kagaku Kenkyusho Co.). Solvent system used was 30%–50% acetonitrile water (linear density gredient). Detection was performed by UV 335 nm and flow rate at 6 ml/min. As the results, K97-0239A substance 4.32 mg and K97-0239B substance 5.80 mg were obtained.

Industrial Applicability

Novel K97-0239 substance of the present invention is low toxicity and specifically inhibits formation of foamed macrophage, consequently, it is expected to be useful for prevention and treatment of arteriosclerosis and diseased caused therefrom.

What is claimed is:

1. A K97-0239 substance comprising K97-0239A substance represented by formula [I]:

and K97-0239B substance represented by formula [II]:

2. A process for production of K97-0239 substance comprising culturing a microorganism belonging to genus *Streptomyces* and having ability to produce K97-0239 substance, accumulating K97-0239 substance in a cultured mass and isolating K97-0239 substance from said cultured mass.

3. The process according to claim 2 wherein a microorganism belonging to genus *Streptomyces* and having ability to produce K97-0239 substance is *Streptomyces* sp. K97-0239 FERM BP-7514.

4. A microorganism belonging to genus *Streptomyces* and having ability to produce K97-0239 substance, and wherein said microorganism is *Streptomyces* sp. K97-0239 FERM BP 7514 and mutant strains thereof.

5. A K97-0239 substance comprising K97-0239A substance represented by formula [I]:

6. A K97-0239 substance comprising K97-0239A substance represented by formula [II]:

* * * * *